(12) United States Patent
Clarke et al.

(10) Patent No.: US 7,390,918 B2
(45) Date of Patent: Jun. 24, 2008

(54) INTEGRATED PROCESS FOR THE MANUFACTURE OF ALKENYL CARBOXYLATES

(75) Inventors: Robert William Clarke, Driffield (GB); Mark Stephen Roberts, Beverley (GB)

(73) Assignee: BB Chemicals Limited, Middlesex (GB)

(*) Notice: Subject to any disclaimer, the term of this patent is extended or adjusted under 35 U.S.C. 154(b) by 295 days.

(21) Appl. No.: 10/500,305

(22) PCT Filed: Dec. 4, 2002

(86) PCT No.: PCT/GB02/05455

§ 371 (c)(1),
(2), (4) Date: Jun. 28, 2004

(87) PCT Pub. No.: WO03/055838

PCT Pub. Date: Jul. 10, 2003

(65) Prior Publication Data

US 2005/0020847 A1    Jan. 27, 2005

(30) Foreign Application Priority Data

Jan. 2, 2002    (GB) .................................. 0200021.4

(51) Int. Cl.
*C07C 67/04* (2006.01)
*C07C 67/48* (2006.01)

(52) U.S. Cl. .................................. 560/247; 560/248

(58) Field of Classification Search ................ 560/231, 560/232, 233; 562/523, 542, 549
See application file for complete search history.

(56) References Cited

U.S. PATENT DOCUMENTS 6,040,474 A    3/2000    Jobson et al.

6,143,921 A * 11/2000 Karim et al. ................ 560/245

FOREIGN PATENT DOCUMENTS

| EP | 0 985 656 A1 | 3/2000 |
|---|---|---|
| WO | WO 01/90042 A1 | 11/2001 |
| WO | WO 01/90043 A1 | 11/2001 |

OTHER PUBLICATIONS

Answer 1 of 1 WPIDS 2002 Thomson Derwent; "Purification of acetic acid—comprises supplying produced gas containing acetic acid to separation tower having distillation tower, supplying azeotropic agent and distillation"; Accession No. 1997-276700 (Abstract).

* cited by examiner

*Primary Examiner*—Karl Puttlitz
(74) *Attorney, Agent, or Firm*—Nixon & Vanderhye

(57) ABSTRACT

An integrated process for the production of an alkenyl carboxylate, such as vinyl acetate which process comprises the steps of (a) contacting in an oxidation reaction zone a $C_2$ to $C_4$ alkane, such as ethane, a molecular oxygen-containing gas, optionally the corresponding alkene and optionally water, in the presence of a catalyst to produce a stream comprising alkene, carboxylic acid and water; (b) separating at least a portion of the stream from step (a) into a fraction comprising the alkene and a fraction comprising the carboxylic acid and water; (c) contacting in a second reaction zone at least a portion of said alkene fraction produced in step (b), a carboxylic acid and a molecular oxygen-containing gas, in the presence of a catalyst to produce a product stream comprising an alkenyl carboxylate, water and carboxylic acid; (d) separating at least a portion of the product stream from step (c) and at least a portion of the carboxylic acid and water fraction produced in step (b) by azeotropic distillation into an overhead fraction comprising the alkenyl carboxylate and a base fraction comprising the carboxylic acid; (e) recovering the alkenyl carboxylate from the overhead fraction separated in step (d).

23 Claims, 1 Drawing Sheet

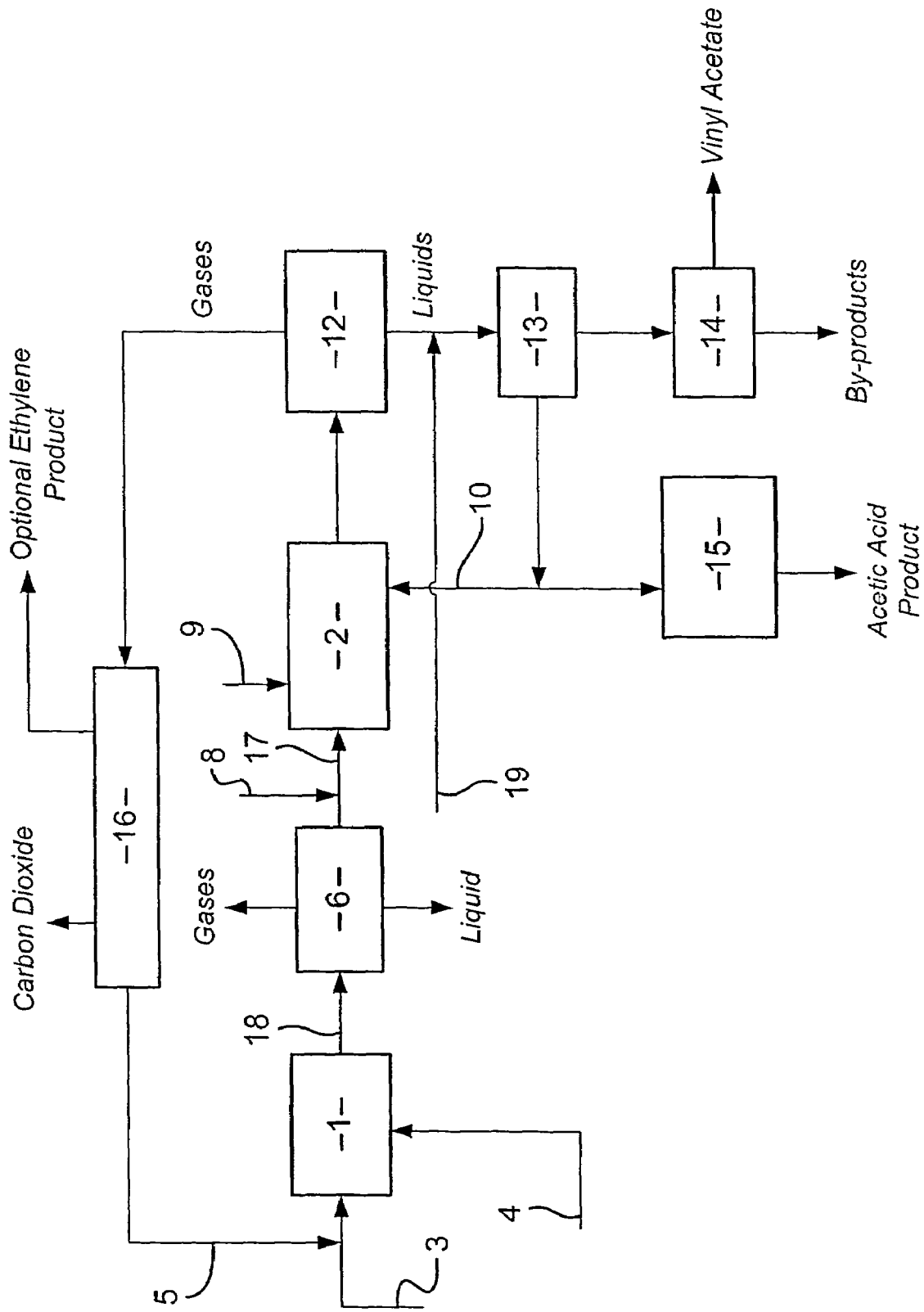

INTEGRATED PROCESS FOR THE MANUFACTURE OF ALKENYL CARBOXYLATES

This application is the U.S. National Phase of International Application PCT/GB02/05455, 4 Dec. 2002, which designated the U.S.

The present invention relates to an integrated process for the oxidation of a $C_2$ to $C_4$ alkane to produce the corresponding alkene and carboxylic acid and wherein the alkene and carboxylic acid are further used as reactants to produce an alkenyl carboxylate.

BACKGROUND OF THE INVENTION

Carboxylic acids are useful feedstocks for the production of alkenyl carboxylates. Thus, for example, acetic acid is used to manufacture vinyl acetate. Acetic acid may be produced by the catalytic oxidation of ethylene and/or ethane. Water is produced as a by-product of the oxidation process. In addition, water (steam) is generally added to the feedstock to improve selectivity to acetic acid.

Vinyl acetate is generally prepared commercially by contacting ethylene and acetic acid with molecular oxygen in the presence of a catalyst active for the production of vinyl acetate. Water is produced as a by-product of the reaction.

The water produced as a by-product and additionally any added water in the afore-mentioned processes must be removed from the product acid and alkenyl carboxylate, necessitating expensive capital expenditure and operating costs.

Integrated processes for producing acetic acid and/or vinyl acetate are known in the art. EP-A-0 877 727 discloses an integrated process for the production of acetic acid and/or vinyl acetate from a gaseous feedstock comprising ethylene and/or ethane. The integrated process comprises a first step wherein ethylene and/or ethane is catalytically oxidised in a first reaction zone to produce a product stream comprising acetic acid and water. The acetic acid stream may be passed directly to a second reaction zone without prior removal of water and contacted therein with a molecular oxygen-containing gas in the presence of a catalyst to produce a second product stream comprising vinyl acetate and water.

Research Disclosure 2244 of 1992 (June) No. 338 describes a process for the oxidation of ethane and/or ethylene to produce acetic acid in which the by-product carbon monoxide is oxidised to carbon dioxide. According to this document, the acetic acid, unreacted ethane (if present) and ethylene is passed with or without carbon dioxide and water removal, to a reactor having a suitable catalyst for the production of ethyl acetate or, with the addition of oxygen, for the production of vinyl acetate.

It is also known from, for example, EP-A-0 985 656 that the introduction of water into a reactor for producing vinyl acetate can adversely affect the selectivity to vinyl acetate product. Thus, in EP-A-0 985 656 which discloses a process for the manufacture of vinyl acetate by combining ethylene, acetic acid and an oxygen-containing gas at elevated temperature in the presence of a catalyst, the liquid by-product stream comprising acetic acid and water is treated to reduce the water content thereof before being recycled to the reactor.

Thus there remains a need for an improved integrated process for the manufacture of an alkenyl carboxylate such as vinyl acetate.

In particular, it would be desirable, if in an integrated process for the production of an alkenyl carboxylate by the oxidation of a $C_2$ to $C_4$ alkane to produce the corresponding alkene and carboxylic acid and wherein the alkene and carboxylic acid are contacted with a molecular oxygen-containing gas to produce the alkenyl carboxylate, to minimise the number of water removal processing steps without adversely affecting the selectivity to alkenyl carboxylate, such as vinyl acetate.

SUMMARY OF THE INVENTION

Accordingly, the present invention provides an integrated process for the production of an alkenyl carboxylate which process comprises the steps:
(a) contacting in an oxidation reaction zone a $C_2$ to $C_4$ alkane, a molecular oxygen-containing gas, optionally the corresponding alkene and optionally water, in the presence of at least one catalyst active for the oxidation of the alkane to the corresponding alkene and carboxylic acid, to produce a first product stream comprising alkene, carboxylic acid and water;
(b) separating at least a portion of the product stream from step (a) into a fraction comprising the alkene and a fraction comprising the carboxylic acid and water;
(c) contacting in a second reaction zone at least a portion of said alkene fraction produced in step (b), a carboxylic acid and a molecular oxygen-containing gas, in the presence of at least one catalyst active for the production of alkenyl carboxylate to produce a second product stream comprising alkenyl carboxylate, water and carboxylic acid;
(d) separating at least a portion of the product stream from step (c) and at least a portion of the carboxylic acid and water fraction produced in step (b) by azeotropic distillation into an overhead fraction comprising alkenyl carboxylate and a base fraction comprising carboxylic acid;
(e) recovering the alkenyl carboxylate from the overhead fraction separated in step (d).

Advantageously, in the process of the present invention, the carboxylic acid/water stream obtained in step (b) and the alkenyl carboxylate/water/carboxylic acid mixture obtained from the second reaction zone are separated in a single distillation means thereby eliminating a need for separate acid/water and alkenyl carboxylate/water/acid separation means and thereby allowing a reduction in capital expenditure.

More advantageously, the process of the present invention also allows a reduction in overall energy requirements to be achieved. Distillative separation of a mixture of alkenyl carboxylate, carboxylic acid and water requires less energy than that required to separate a mixture of carboxylic acid and water by distillation.

Furthermore, in avoiding feeding a product stream containing water from the oxidation reaction zone directly to a reactor for producing alkenyl carboxylate, good selectivity to alkenyl carboxylate may be achieved.

By carrying out the separation of carboxylic acid/water and alkenyl carboxylate/water/carboxylic acid mixtures in a single distillation column, the total amount of water in the column is much larger than would be typically present in the separation of alkenyl carboxylate/water/carboxylic acid alone. Surprisingly, in the case where the alkane is ethane and the corresponding carboxylic acid is acetic acid, it has been found that the larger amounts of water enables improved removal of the by-product, ethyl acetate, formed in step (c) to be achieved.

Each of the alkane, molecular oxygen-containing gas, alkene and water may be introduced into the oxidation reaction zone as fresh feed and/or recycle component.

In the present invention, preferably, the $C_2$ to $C_4$ alkane is ethane, the corresponding alkene being ethylene and the corresponding carboxylic acid being acetic acid. The ethylene and acetic acid are reacted with a molecular oxygen-containing gas to produce vinyl acetate.

Typically, the oxidation reaction is performed heterogeneously with solid catalysts and the reactants in the fluid phase. In this case, the concentrations of alkene and optional water may be controlled as partial pressures in the oxidation reaction zone.

Catalysts active for the oxidation of alkane to alkene and carboxylic acid may comprise any suitable catalysts known in the art, for example, for the oxidation of ethane to ethylene and acetic acid as described in U.S. Pat. No. 4,596,787, EP-A-0407091, DE 19620542, WO 99/20592, DE 19630832, WO 98/47850, WO 99/51339, EP-A-0 1043064, WO 9913980, U.S. Pat. Nos. 5,300,682 and 5,300,684, the contents of which are hereby incorporated by reference.

U.S. Pat. No. 4,596,787 relates to a process for the low temperature oxydehydrogenation of ethane to ethylene using a catalyst having the empirical formula $Mo_aV_bNb_cSb_dX_e$ as therein defined, the elements being present in combination with oxygen.

EP-A-0407091 relates to process and catalyst for the production of ethylene and/or acetic acid by oxidation of ethane and/or ethylene in the presence of an oxidation catalyst comprising molybdenum, rhenium and tungsten.

DE 19620542 relates to molybdenum, palladium, rhenium based oxidation catalysts for the production of acetic acid from ethane and/or ethylene.

WO 99/20592 relates to a method of selectively producing acetic acid from ethane, ethylene or mixtures thereof and oxygen at high temperature in the presence of a catalyst having the formula $Mo_aPd_bX_cY_d$ wherein X represents one or several of Cr, Mn, Nb, Ta, Ti, V, Te and W; Y represents one or several of B, Al, Ga, In, Pt, Zn, Cd, Bi, Ce, Co, Rh, Ir, Cu, Ag, Au, Fe, Ru, Os, K, Rb, Cs, Mg, Ca, Sr, Ba, Nb, Zr, Hf, Ni, P, Pb, Sb, Si, Sn, Tl and U and a=1, b=0.0001 to 0.01, c=0.4 to 1 and d=0.005 to 1.

German patent application DE 196 30 832 A1 relates to a similar catalyst composition in which a=1, b>0, c>0 and d=0 to 2. Preferably, a=1, b=0.0001 to 0.5, c=0.1 to 1.0 and d=0 to 1.0.

WO 98/47850 relates to a process for producing acetic acid from ethane, ethylene or mixtures thereof and a catalyst having the formula $W_aX_bY_cZ_d$ in which X represents one or several of Pd, Pt, Ag and Au, Y represents one or several of V, Nb, Cr, Mn, Fe, Sn, Sb, Cu, Zn, U, Ni, and Bi and Z represents one or several of Li, Na, K, Rb, Cs, Be, Mg, Ca, Sr, Ba, Sc, Y, La, Ti, Zr, Hf, Ru, Os, Co, Rh, Ir, B, Al, Ga, In, Tl, Si, Ge, Pb, P, As and Te, a=1, b>0, c>0 and d is 0 to 2.

WO 99/51339 relates to a catalyst composition for the selective oxidation of ethane and/or ethylene to acetic acid which composition comprises in combination with oxygen the elements $Mo_aW_bAg_cIr_dX_eY_f$ wherein X is the elements Nb and V; Y is one or more elements selected from the group consisting of Cr, Mn, Ta, Ti, B, Al, Ga, In, Pt, Zn, Cd, Bi, Ce, Co, Rh, Cu, Au, Fe, Ru, Os, K, Rb, Cs, Mg, Ca, Sr, Ba, Zr, Hf, Ni, P, Pb, Sb, Si, Sn, Tl, U, Re and Pd; a, b, c, d, e and f represent the gram atom ratios of the elements such that $0<a \leq 1$, $0 \leq b<1$ and $a+b=1; 0<(c+d) \leq 0.1$; $0<e \leq 2$; and $0 \leq f \leq 2$.

EP-A-1043064 relates to a catalyst composition for the oxidation of ethane to ethylene and/or acetic acid and/or for the oxidation of ethylene to acetic acid which composition comprises in combination with oxygen the elements molybdenum, vanadium, niobium and gold in the absence of palladium according to the empirical formula: $Mo_aW_bAu_cV_dNb_eY_f$ wherein Y is one or more elements selected from the group consisting of: Cr, Mn, Ta, Ti, B, Al, Ga, In, Pt, Zn, Cd, Bi, Ce, Co, Rh, Ir, Cu, Ag, Fe, Ru, Os, K, Rb, Cs, Mg, Ca, Sr, Ba, Zr, Hf. Ni, P, Pb, Sb, Si, Sn, Tl, U, Re, Te, and La; a, b, c, d, e and f represent the gram atom ratios of the elements such that: $0<a \leq 1$; $0 \leq b<1$ and $a+b=1$; $10^{-5}<c \leq 0.02$; $0<d \leq 2$; $0<e \leq 1$; and $0 \leq f \leq 2$.

WO 99/13980 relates to a catalyst for the selective oxidation of ethane to acetic acid of formula: $Mo_aV_bNb_cX_d$ wherein X is at least one promoter element selected from the group consisting of P, B, Hf, Te and As; a is a number ranging from about 1 to about 5; b is 1; c is a number ranging from about 0.01 to about 0.5; and d is a number ranging from greater than 0 to about 0.1.

U.S. Pat. No. 5,300,682 relates to the use of oxidation catalyst with empirical formula of $VP_aM_bO_x$ where M is one or more of Co, Cu, Re, Fe, Ni, Nb, Cr, W, U, Ta, Ti, Zr, Hf, Mn, Pt, Pd, Sn, Sb, Bi, Ce, As, Ag and Au, a is 0.5 to 3, b is 0 1 and x satisfies the valence requirements.

U.S. Pat. No. 5,300,684 relates to a fluid bed oxidation reaction using for example $Mo_{0.37}Re_{0.25}V_{0.26}Nb_{0.07}Sb_{0.03}Ca_{0.02}O_x$.

Other suitable oxidation catalysts for use in the present invention are described in WO 99/13980 which relates to the use of catalysts with elements in combination with oxygen in the relative gram atom ratios of $Mo_aV_bNb_cX_d$ where X=P, B, Hf, Te or As; U.S. Pat. No. 6,030,920 which relates to the use of catalysts with elements in combination with oxygen in the relative gram atom ratios of $Mo_aV_bNb_cPd_d$; WO 00/00284 which relates to the use of catalysts with elements in combination with oxygen in the relative gram atom ratios of $Mo_aV_bNb_cPd_d$ and/or $Mo_aV_bLa_cPd_d$; U.S. Pat. No. 6,087,297 which relates to the use of catalysts with elements in combination with oxygen in the relative gram atom ratios of $Mo_aV_bPd_cLa_d$; WO 00/09260 which relates to the use of catalysts with elements in combination with oxygen in the relative gram atom ratios of $Mo_aV_bLa_cPd_dNb_eX_f$ where X=Cu or Cr and e and f can be zero; WO 00/29106 and WO 00/29105 which relate to the use of catalysts with elements in combination with oxygen in the relative gram atom ratios of $Mo_aV_bG_cP_dNb_eX_f$ wherein X=La, Te, Ge, Zn, Si, In or W and WO 00/38833 which relates to the use of catalysts with elements in combination with oxygen in the relative gram atom ratios of $Mo_aV_bLa_cPd_dNb_eX_f$ wherein X=Al, Ga, Ge or Si, the contents of which are hereby incorporated by reference.

Solid catalysts active for the oxidation of the $C_2$ to $C_4$ alkane may be supported or unsupported. Examples of suitable supports include silica, diatomaceous earth, montmorillonite, alumina, silica alumina, zirconia, titania, silicon carbide, activated carbon and mixtures thereof.

Solid catalysts active for the oxidation of the $C_2$ to $C_4$ alkane may be used in the form of a fixed or fluidised bed.

The oxidation catalyst would be expected to oxidise at least part of any alkene fed to the oxidation reaction zone, for example to the corresponding carboxylic acid.

The molecular oxygen-containing gas used in the oxidation reaction zone, may be air or a gas richer or poorer in molecular oxygen than air. A suitable gas may be, for example, oxygen diluted with a suitable diluent, for example nitrogen or carbon dioxide. Preferably, the molecular oxygen-containing gas is oxygen. Preferably, at least some of the molecular oxygen-containing gas is fed to the oxidation reaction zone independently from the alkane and optional alkene feeds, and any recycle streams.

The alkane and alkene fed into the oxidation reaction zone of the process of the present invention may be substantially pure or may be admixed, for example, with one or more of nitrogen, argon, methane, carbon dioxide, carbon monoxide, hydrogen, and low levels of other $C_2$-$C_4$ alkenes/alkanes.

Suitably, the concentration of alkene (as fresh feed and/or recycle component) is from 0 and up to and including 50 mol % of the total feed, including recycles, to the oxidation reaction zone, preferably from 1 to 20 mol %, more preferably from 1 to 15 mol %.

Suitably, the concentration of water (as fresh feed and/or recycle component) is from 0 to 50 mol % inclusive of the total feed, including recycles, to the oxidation reaction zone, preferably from 0 to 25 mol %.

In a preferred embodiment of the present invention, an alkene, such as ethylene, and water are co-fed into the oxidation reaction zone.

Suitably, the alkene, for example, ethylene, and water may be used in a ratio of 1:0.1-250 by weight, such as 1:0.1-100 or 1:0.1-50 but preferably in a ratio 1:0.1-10 by weight.

When solid catalysts are used in the oxidation reaction zone, the alkane, the optional corresponding alkene, molecular-oxygen containing gas, optional water and any recycle gases are preferably passed through the oxidation reaction zone with a residence time corresponding to a combined gas hourly space velocity (GHSV) of 500-10,000 $hr^{-1}$; the GHSV being defined as volume (calculated at STP) of gas passing through the reactor divided by the bulk volume of settled catalyst.

The oxidation reaction of the present invention may suitably be carried out at a temperature in the range from 100 to 400° C., typically in the range 140 to 350° C.

The oxidation reaction of the present invention may suitably be carried out at atmospheric or superatmospheric pressure, for example, in the range from 80 to 400 psig. (0.65 to 2.86 Mpa).

Typically, alkane conversions in the range 1 to 99% may be achieved in the oxidation reaction of the present invention.

Typically, oxygen conversions in the range 30 to 100% may be achieved in the oxidation reaction of the present invention.

In the oxidation reaction of the present invention, the catalyst suitably has a productivity in the range 10to 10000 grams of carboxylic acid, such as acetic acid, per hour per kilogram of catalyst.

Carbon monoxide can have an adverse effect on some catalysts used in the production of vinyl acetate. Thus, depending on the nature of the catalyst employed, it is desirable that the first product stream should have a low concentration of carbon monoxide by-product, Thus, it is also preferred to use a catalyst in the oxidation reaction zone that gives negligible carbon monoxide by-product. An additional catalyst component in the oxidation reaction zone may be used to oxidise carbon monoxide to carbon dioxide. The additional catalyst component may be present in the oxidation catalyst or catalysts or in a secondary reaction zone.

When ethane is used as a reactant for the oxidation process, the product stream comprises acetic acid, ethylene and water, and may also contain ethane and oxygen, inert gas components such as argon and nitrogen and the by-products, acetaldehyde, carbon monoxide and carbon dioxide. Acetaldehyde and carbon monoxide may be converted by the molecular oxygen-containing gas to produce acetic acid and carbon dioxide respectively, either in downstream processes or, after recycling, in the oxidation reaction zone.

Ethylene is present in the product stream of the oxidation reaction as unconverted reactant ethylene from the feed and/ or as oxidation product of the ethane reactant.

The product stream from the oxidation process is separated in one or more stages into a fraction comprising the alkene and a fraction comprising the carboxylic acid and water. Any suitable separation means may be employed such as membrane separation, condensation or distillation. Preferably, the separation is carried out by condensation.

Where the product stream from the oxidation process comprises acetic acid, ethylene and water, this may be separated by condensation into an overhead fraction comprising ethylene and a base fraction comprising acetic acid and water.

Suitably, the weight ratio of water:acid in the acid/water fraction is in the range from 10:1 to 0.5:1, preferably in the range 5:1 to 0.5:1, especially in the range 2:1 to 0.5:1.

Carboxylic acid and/or alkene may be optionally recovered from the product of the oxidation process.

The alkene fraction from the separation stage is fed, as one or more streams, to a second reaction zone together with optional additional molecular oxygen-containing gas, optional additional alkene and carboxylic acid to produce alkenyl carboxylate, such as vinyl acetate.

Unconverted alkane and/or alkene may be recycled together or after at least partial separation from the downstream process to the oxidation reaction zone directly or indirectly after one or more separation stages.

Catalysts known in the art for the production of alkenyl carboxylates may be used in the process of the present invention. Thus, catalyst active for the production of vinyl acetate which may be used in a second reaction zone of the present invention may comprise, for example, catalysts as described in GB 1 559 540; U.S. Pat. No. 5,185,308 and EP-A-0672453 the contents of which are hereby incorporated by reference.

GB 1 559 540 describes a catalyst active for the preparation of vinyl acetate by the reaction of ethylene, acetic acid and oxygen, the catalyst consisting essentially of: (1) a catalyst support having a particle diameter of from 3 to 7 nun and a pore volume of from 0.2 to 1.5 ml/g, a 10% by weight water suspension of the catalyst support having a pH from 3.0 to 9.0, (2) a palladium-gold alloy distributed in a surface layer of the catalyst support, the surface layer extending less than 0.5 mm from the surface of the support, the palladium in the alloy being present in an amount of from 1.5 to 5.0 grams per liter of catalyst, and the gold being present in an amount of from 0.5 to 2.25 grams per liter of catalyst, and (3) from 5 to 60 grams per liter of catalyst of alkali metal acetate.

U.S. Pat. No. 5,185,308 describes a shell impregnated catalyst active for the production of vinyl acetate from ethylene, acetic acid and an oxygen containing gas, the catalyst consisting essentially of: (1) a catalyst support having a particle diameter from about 3 to about 7 mm and a pore volume of 0.2 to 1.5 ml per gram, (2) palladium and gold distributed in the outermost 1.0 mm thick layer of the catalyst support particles, and (3) from about 3.5 to about 9.5% by weight of potassium acetate wherein the gold to palladium weight ratio in said catalyst is in the range 0.6 to 1.25.

EP-A-0672453 describes palladium containing catalysts and their preparation for fluid bed vinyl acetate processes.

An advantage of using a palladium-containing catalyst is that any carbon monoxide produced in the first reaction zone will be consumed in the presence of oxygen and the palladium-containing catalyst in the second reaction zone, thereby eliminating the need for a separate carbon monoxide removal reactor.

Typically, the production of alkenyl carboxylate such as vinyl acetate in the second reaction zone is carried out heterogeneously with the reactants being present in the gas phase.

Additional alkene reactant may be fed to the second reaction zone for the production of alkenyl carboxylate as well as the alkene from the oxidation reaction zone as oxidation product and/or unconsumed alkene reactant.

Additional alkene introduced into the second reaction zone for the production of alkenyl carboxylate may be substantially pure or may be admixed, for example, with one or more of nitrogen, argon, methane, carbon dioxide, carbon monoxide, hydrogen, and low levels of other $C_2$-$C_4$ alkenes/alkanes.

The molecular oxygen-containing gas used in the second reaction zone for the production of alkenyl carboxylate may comprise unreacted molecular oxygen-containing gas from step (a) and/or additional molecular oxygen-containing gas.

The additional molecular oxygen-containing gas, if used, may be air or a gas richer or poorer in molecular oxygen than air. A suitable additional molecular oxygen-containing gas may be, for example, oxygen diluted with a suitable diluent, for example nitrogen or carbon dioxide. Preferably, the additional molecular oxygen-containing gas is oxygen. Preferably, at least some of the molecular oxygen-containing gas is fed independently to the second reaction zone from the alkene and carboxylic acid reactants.

The carboxylic acid fed to the second reaction zone, may be any carboxylic acid or a mixture of carboxylic acids, but is preferably, the corresponding carboxylic acid of the alkene employed in the second reaction zone.

Where the alkene used in the second reaction zone is ethylene, the carboxylic acid used is preferably, acetic acid.

The carboxylic acid fed to the second reaction zone for the production of alkenyl carboxylate may comprise fresh and/or recycle acid.

The fresh and recycle carboxylic acid may be introduced into the second reaction zone either as separate feed streams or as a single feed stream comprising both fresh and recycle acid.

The carboxylic acid fed to the second reaction zone for the production of alkenyl carboxylate may comprise at least a portion of the acid obtained from downstream processes such as from the separation of the acid from a mixture of the acid/alkenyl carboxylate/water.

The carboxylic acid fed to the second reaction zone, such as acetic acid, has a water content such that the amount of water entering the second reaction zone preferably comprises less than 6 wt %, more preferably less than 4 wt %, especially less than 3 wt % of the total carboxylic acid and water entering the second reaction zone.

At least part of the carboxylic acid fed to the second reaction zone may be liquid.

When solid catalysts are used in the second reaction zone for the production of alkenyl carboxylate, the product from the oxidation reaction zone, ally additional alkene or carboxylic acid reacts, any recycle streams and molecular oxygen-containing gas are preferably passed through the second reaction zone at a combined gas hourly space velocity (GHSV) of 500 to 10,000 $hr^{-1}$.

The second reaction zone for the production of alkenyl carboxylate may stably be operated at a temperature in the range from 140 to 200° C.

The second reaction zone for the production of alkenyl carboxylate may suitably be operated at a pressure in the range 50 to 300 psig. (0.44 to 2.17 Mpa).

The second reaction zone for the production of alkenyl carboxylate may suitably be operated as either a fixed or a fluidised bed process.

Carboxylic acid conversions in the range 5 to 80% may be achieved in the second reaction zone for the production of alkenyl carboxylate.

Oxygen conversions in the range 20 to 100% may be achieved in the second reaction zone for the production of alkenyl carboxylate.

Alkene conversions in the range 3 to 100% may be achieved in the second reaction zone for the production of alkenyl carboxylate.

In the second reaction zone for the production of alkenyl carboxylate, the catalyst suitably has a productivity in the range 10 to 10000 grams of alkenyl carboxylate per hour per kg of catalyst.

The product stream from the second reaction zone comprises alkenyl carboxylate, water and carboxylic acid. At least a portion of the product stream from the second reaction zone is fed together with at least a portion of the carboxylic acid and water fraction obtained from the separation of the product stream from the oxidation reaction zone, to a distillation column for separation of the carboxylic acid from the alkenyl carboxylate and water.

At least a portion of the product stream from the oxidation reaction zone may be co-joined with at least a portion of the product stream from the second reaction zone and the co-joined stream fed, as one or more streams, into the distillation column. Alternatively or additionally, at least a portion of the product stream from the oxidation reaction zone may be fed, as one or more streams, into the distillation column separately from the product stream from the second reaction zone. At least a portion of the product stream from the second reaction zone may be fed, as one or more streams, into the distillation column.

Distillative separation of the product stream from the second reaction zone and the carboxylic acid and water fraction obtained from the separation of the product stream from the oxidation reaction zone produces an overhead fraction comprising alkenyl carboxylate and a base fraction comprising carboxylic acid.

The carboxylic acid base fraction also comprises water. The number of plates within the distillation column may be selected according to the desired reduction in water concentration in the carboxylic acid base fraction. The carboxylic acid/water mixture may be withdrawn from the base of the distillation column either in liquid or vapour form.

When the alkane used in the process of the present invention is ethane, the product stream from the second reaction zone for the production of alkenyl carboxylate may comprise vinyl acetate, water and acetic acid and optionally also unreacted ethylene, ethane, acetaldehyde, nitrogen, argon, carbon monoxide and carbon dioxide. The carboxylic acid and water fraction obtained from the separation of the product stream from the oxidation reaction zone will comprise acetic acid and water. The vinyl acetate, water and acetic acid stream from the second reaction zone may be introduced separately from or as a single feed stream with the acetic acid and water fraction into the distillation column wherein the stream(s) is/are separated by azeotropic distillation into an overhead fraction comprising vinyl acetate and water and a base fraction comprising acetic acid and water. The base fraction may be removed from the distillation column as liquid from the bottom of the column, or as a vapour one or more stages above the bottom of the column.

In a preferred embodiment of the process of the present invention, the product stream from the second reaction zone is separated in one or more stages into a gaseous fraction comprising unreacted alkene and a liquid fraction comprising alkenyl carboxylate, carboxylic acid and water.

Any suitable separation means may be employed such as membrane separation, condensation or distillation. Preferably, condensation is employed.

Thus, where the second product stream comprises vinyl acetate, water and acetic acid, a gaseous fraction comprising ethylene, ethane, acetaldehyde, carbon monoxide and carbon dioxide, if any, may be removed from the second product stream, as an overhead from a scrubbing column, in which a liquid fraction comprising vinyl acetate, water and acetic acid is removed from the base. The ethylene and/or ethane may be recycled to step (a) and/or step (c).

The alkenyl carboxylate, for example, vinyl acetate is recovered from the overhead fraction, suitably, for example, by decantation. The recovered alkenyl carboxylate, such as vinyl acetate, may, if desired, be further purified in a known manner.

The base fraction comprising carboxylic acid, such as acetic acid, and water may be recycled, with or preferably without further purification, to step (c) of the process. Alternatively, the carboxylic acid is recovered from the base fraction and may be further purified if desired, in known manner, for example by distillation.

BRIEF DESCRIPTION OF THE DRAWING

The invention will now be illustrated with reference to the Figure and the Example.

FIG. 1 represents in schematic block-diagram, apparatus suitable for use in the process of the present invention.

DETAILED DESCRIPTION OF THE PREFERRED EMBODIMENTS

The apparatus comprises an oxidation reaction zone (1) provided with a supply of ethane and optionally ethylene (3), a supply of a molecular oxygen-containing gas (4), a supply of recycle gas comprising ethane and optionally ethylene (5) an outlet (18) for a first product stream into a separation means (6) for separating the first product stream into an ethylene fraction and an acetic acid and water fraction. Depending on the scale of the process, the oxidation reaction zone (1) may comprise either a single reactor or several reactors in parallel or series.

The apparatus also comprises a second reaction zone (2) for acetoxylation of ethylene to vinyl acetate which is provided with means (17) for conveying at least a portion of the ethylene fraction from the separation means (6) into the second reaction zone, a supply of molecular oxygen-containing gas (9), a supply of recycle acetic acid (10) and an optional supply or supplies of ethylene and/or acetic acid (8). Depending on the scale of the process, the second reaction zone (2) may comprise either a single reactor or several reactors in parallel or in series.

The apparatus further comprises an optional scrubber (12) for the product from the second reaction zone; distillation means (13) for separating acetic acid/vinyl acetate/water from the product of the second reaction zone and the acetic acid and water fraction from separation means (6); vinyl acetate purification means (14); optional acetic acid purification means (15) and one or more optional separation means (16) for separating carbon dioxide from recycle gases from the second reaction zone and optionally for recovery of ethylene product In use, the oxidation reaction zone (1) is provided with at least one catalyst each active for the oxidation of the ethane to form acetic acid and ethylene. Suitably the oxidation catalysts are solid catalysts. Molecular oxygen-containing gas is fed to the oxidation reaction zone (1) from supply (4) through one or more inlets. A gaseous feedstock comprising ethane, and optionally ethylene is fed to the oxidation reaction zone (1) from supply (3). Recycle gas comprising ethane and optionally ethylene is also fed to the oxidation reactor from supply (5). The molecular oxygen-containing gas, ethane and recycle gas are introduced into the oxidation reaction zone (1) through one or more inlets separately or in partial or complete combination. Optionally at least one of the streams fed to the oxidation reactor also comprises water.

In the oxidation reactor a first product stream is produced which comprises ethylene (as product and/or unreacted feed), acetic acid, water, optionally unconsumed molecular oxygen-containing gas and by-products such as carbon monoxide, carbon dioxide, inerts and acetaldehyde. At least a portion of this product stream is passed to separation means (6), such as a scrubber, from which a gaseous fraction comprising ethylene and a liquid fraction comprising acetic acid and water are removed. At least a portion of the liquid fraction comprising the acetic acid and water is co-joined through supply line (19) with the vinyl acetate/water/acetic acid liquid stream from scrubber (12). Although not shown, at least a portion of the acetic/water fraction from separation means (6) may be fed directly to distillation means (13) separately from the vinyl acetate/water/acetic acid stream. Additionally, acetic acid may be recovered from a portion of the liquid fraction, for example, by distillation.

At least a portion of the ethylene fraction from separation means (6) is fed by means (17) into the second reaction zone which is provided with an acetoxylation catalyst, suitably a solid catalyst. At least a portion of the ethylene fraction may be fed directly into the second reaction zone. Alternatively, prior to being fed into the second reaction zone, the at least a portion of the ethylene fraction may be separated by suitable separation means (not shown) from by-products such as carbon dioxide. Additionally, part of the ethylene fraction may be recycled, with or without by-product separation to the oxidation reaction zone. If desired, ethylene product may be recovered from a portion of the fraction, by methods known in the art.

A molecular oxygen-containing gas is fed to the second reaction zone from supply (9). Acetic acid is fed to the second reaction zone from recycle supply (10). Optionally, additional ethylene and/or acetic acid may be fed to the second reaction zone from supply or supplies (8). The ethylene fraction, molecular oxygen-containing gas, recycle acetic acid and optional additional supplies of ethylene and/or acetic acid are fed into the second reaction zone through one or more inlets separately or in partial or complete combination.

In the second reaction zone the ethylene, acetic acid and molecular oxygen react to produce a second product stream comprising vinyl acetate.

The second reaction product is passed to scrubber (12) from which gas and liquid are separated. Carbon dioxide is separated from the gas and optionally ethylene product recovered, in one or more separation stages (16) by methods known in the art. The remaining ethylene and ethane may be recycled to the first and/or second reactors. The acetic acid/water fraction obtained from separation means (6) is co-joined via supply means (19) with the scrubber liquid stream. Acetic acid is separated from the co-joined scrubber liquid and the acetic acid/water fraction by azeotropic distillation in distillation column (13). The acetic acid obtained as a base fraction from the distillation column (13) is recycled to the second reaction zone; Optionally, acetic acid product may be recovered from the recycle stream by means (15), for example by distillation. The overhead from the distillation column (13) comprises a vinyl acetate and water. Vinyl acetate product is recovered from the overhead from the means (14), for example by distillation.

Experiment 1

A Model (A) was run using standard three phase distillation equations in ASPEN plus to simulate the azeotropic distillation in a distillation column of a feed Stream (i). Stream (i) comprised the components vinyl acetate, water and acetic acid. The overhead from the distillation column was passed to a condenser from which was removed a vapour stream and a liquid stream. The liquid stream comprising vinyl acetate was passed to a decanter. The vinyl acetate product was recovered from the organic phase of the decanter. The base stream from the distillation column was defined to comprise approximately 95 wt % acetic acid, 5 wt % water and 19 ppm vinyl acetate. A stream comprising ethyl acetate was removed as a side draw from the distillation column. An inhibitor to prevent polymerization of the vinyl acetate was fed into the top of the distillation column.

The Model used a distillation column having 42 theoretical stages with a condenser temperature of 35 C and a reboiler temperature of 126.3 C. Nitrogen was used to represent the non-condensable components (ethylene, ethane, carbon dioxide, carbon monoxide, argon, and oxygen).

The reflux rate, and the ethyl acetate side draw and vinyl acetate product stream flow rates for Model (A) are given in Table 1. The composition of the streams is given in Table 2.

EXAMPLE 1

Model (B)

Model (A) was repeated except that the feed stream to the distillation column was a combined stream of Stream (i) and a Stream (ii). Stream (ii) comprised the components acetic acid and water.

The flow rates of the ethyl acetate side draw and vinyl acetate product streams and reflux rate are given in Table 1. Stream compositions are given in Table 3.

TABLE 1

|  | Model (A) kmol/hr | Model (B) kmol/hr |
| --- | --- | --- |
| Reflux rate | 1975.00 | 8571.43 |
| Side draw rate | 2.3142 | 2.3143 |
| Vinyl acetate Product rate | 372.717 | 368.454 |

TABLE 2

| Component | Units | Feed Stream | Decanter Aqueous Stream | Vinyl Acetate Product Stream | Column Side draw stream | Condenser Vapour Stream | Column Base Stream | Inhibitor (200 kg/hr) |
| --- | --- | --- | --- | --- | --- | --- | --- | --- |
| Water | kg/hr | 13016 | 8103.4 | 318.8 | 12.9 | 42.3 | 4539 |  |
| Acetic acid | kg/hr | 86223 | 0 | 0 | 19.1 | 0 | 86204 |  |
| VAM | kg/hr | 31283 | 101.6 | 30460 | 91.7 | 822.9 | 1.8 | 195.7 |
| Ethyl acetate | kg/hr | 25 | 0.14 | 0.46 | 19.1 | 0.008 | 5.35 |  |
| Nitrogen | kg/hr | 975.9 | 16.7 | 33.5 | 0 | 925.9 | 0 |  |

TABLE 3

| Component | Units | Feed Stream | Decanter Aqueous Stream | Vinyl Acetate Product Stream | Column Side draw Stream | Condenser Vapour Stream | Column Base Stream | Inhibitor (200 kg/hr) |
| --- | --- | --- | --- | --- | --- | --- | --- | --- |
| Water | kg/hr | 55259 | 44579 | 315.1 | 12.63 | 35.1 | 10317 |  |
| Acetic acid | kg/hr | 196000 | 0 | 0 | 4.1 | 0 | 195990 |  |
| VAM | kg/hr | 31283 | 559.1 | 30113 | 119.51 | 683.5 | 3.94 | 195.7 |
| Ethyl acetate | kg/hr | 25 | 0.011 | 0.006 | 13.8 | 0 | 11.18 |  |
| Nitrogen | kg/hr | 893.89 | 91.86 | 33.15 | 0 | 768.89 | 0 |  |

From a comparison of Tables 2 and 3 it can clearly be seen that by feeding in a combined stream of vinyl acetate, acetic acid and water (Stream (i)) and a stream of acetic acid and water (Stream (ii)), the concentration of ethyl acetate byproduct in the vinyl acetate product stream is significantly reduced.

The invention claimed is:

1. An integrated process for the production of an alkenyl carboxylate which process comprises the steps of:
    (a) contacting in an oxidation reaction zone a $C_2$ to $C_4$ alkane, a molecular oxygen-containing gas, optionally the corresponding alkene and optionally water, in the presence of at least one catalyst active for the oxidation of the alkane to the corresponding alkene and carboxylic acid, to produce a first product stream comprising alkene, carboxylic acid and water;
    (b) separating at least a portion of the product stream from step (a) into a fraction comprising the alkene and a fraction comprising the carboxylic acid and water;
    (c) contacting in a second reaction zone at least a portion of said alkene fraction produced in step (b), a carboxylic acid and a molecular oxygen-containing gas, in the presence of at least one catalyst active for the production of alkenyl carboxylate to produce a second product stream comprising alkenyl carboxylate, water and carboxylic acid;

(d) feeding the carboxylic acid and water fraction produced in step (b) and the product stream comprising alkenyl carboxylate, water and carboxylic acid from step (c) to a single distillation means;

(e) performing azeotropic distillation in said single distillation means to separate the product stream from step (c) and at least a portion of the carboxylic acid and water fraction produced in step (b) by azeotropic distillation in said single distillation means into an overhead fraction comprising alkenyl carboxylate and a base fraction comprising carboxylic acid;

(f) recovering the alkenyl carboxylate from the overhead fraction separated in step (d).

2. A process according to claim 1 wherein the at least a portion of the product stream from the second reaction zone is introduced separately from or as a single feed stream with the at least a portion of the carboxylic acid/water fraction obtained in step (b) to the distillation column.

3. A process according to claim 1 wherein at least a portion of the product stream from the oxidation reaction zone is co-joined with at least a portion of the product stream from the second reaction zone and the co-joined stream is fed into the distillation column.

4. A process according to claim 3 wherein the co-joined stream is fed as one or more streams into the distillation column.

5. A process according to claim 3 wherein at least a portion of the product stream from the oxidation reaction zone is fed to the distillation column separately from the product stream from the second reaction zone.

6. A process according to claim 4 wherein at least a portion of the product stream from the oxidation reaction zone is fed to the distillation column separately from the product stream from the second reaction zone.

7. A process according to claim 5 wherein the product stream from the oxidation reaction zone is fed as one or more streams to the distillation column.

8. A process according to claim 6 wherein the product stream from the oxidation reaction zone is fed as one or more streams to the distillation column.

9. A process according to claim 5 wherein the product stream from the second reaction zone is fed as one or more streams to the distillation column.

10. A process according to claim 6 wherein the product stream from the second reaction zone is fed as one or more streams to the distillation column.

11. A process according to claim 7 wherein the product stream from the second reaction zone is fed as one or more streams to the distillation column.

12. A process according to claim 8 wherein the product stream from the second reaction zone is fed as one or more streams to the distillation column.

13. A process according to claim 1 wherein the alkenyl carboxylate is vinyl acetate, the $C_2$ to $C_4$ alkane is ethane, the product stream from the oxidation reaction zone comprises ethylene, acetic acid and water, the carboxylic acid fed to the second reaction zone is acetic acid and the product stream from the second reaction zone comprises vinyl acetate, acetic acid and water.

14. A process according to claim 13 wherein ethylene and water are fed to the oxidation reaction zone.

15. A process according to claim 1 wherein the alkene fraction from the separation stage (b) is fed to the second reaction zone together with additional alkene.

16. A process according to claim 15 wherein the additional alkene is ethylene.

17. A process according to claim 1 wherein the weight ratio of water: carboxylic acid in the carboxylic acid/water fraction obtained in step (b) is in the range from 10:1 to 0.5:1.

18. A process according to claim 1 wherein the carboxylic acid fed to the second reaction zone has a water content, such that the amount of water entering the second reaction zone comprises less than 6% by weight of the total carboxylic acid and water entering the second reaction zone.

19. A process according to claim 1 wherein the catalyst in the oxidation reaction zone is supported or unsupported.

20. A process according to claim 1 wherein the catalyst in the oxidation reaction zone is used in the form of a fixed bed or a fluidized bed.

21. A process according to claim 1 wherein the concentration of alkene fed to the oxidation reaction zone is from 0 and up to and including 50 mol % of the total feed, including recycles.

22. A process according to claim 1 wherein the concentration of water fed to the oxidation reaction zone is from 0 and up to and including 50 mol % of the total feed, including recycles.

23. A process according to claim 1 wherein the product stream from the second reaction zone is separated in one or more stages into a gaseous fraction comprising unreacted alkene and a liquid fraction comprising alkenyl carboxylate, carboxylic acid and water.

* * * * *

UNITED STATES PATENT AND TRADEMARK OFFICE
CERTIFICATE OF CORRECTION

PATENT NO. : 7,390,918 B2 Page 1 of 1
APPLICATION NO. : 10/500305
DATED : June 24, 2008
INVENTOR(S) : Clarke et al.

It is certified that error appears in the above-identified patent and that said Letters Patent is hereby corrected as shown below:

Title page, item "(73) Assignee", delete "BB Chemicals Limited, Middlesex (GB)" and insert --BP Chemicals Limited, Middlesex (GB)--

Signed and Sealed this

Twelfth Day of August, 2008

JON W. DUDAS
*Director of the United States Patent and Trademark Office*